(12) United States Patent
Shields et al.

(10) Patent No.: US 10,314,591 B2
(45) Date of Patent: Jun. 11, 2019

(54) MEDICAL DEVICE AND CORRESPONDING METHOD OF USE FOR ARTERIOVENOUS FISTULA CREATION

(71) Applicant: Cook Medical Technologies LLC, Bloomington, IN (US)

(72) Inventors: Adam Shields, Lafayette, IN (US); Keith R. Milner, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 205 days.

(21) Appl. No.: 15/228,895

(22) Filed: Aug. 4, 2016

(65) Prior Publication Data

US 2017/0035423 A1 Feb. 9, 2017

Related U.S. Application Data

(60) Provisional application No. 62/200,897, filed on Aug. 4, 2015.

(51) Int. Cl.
*A61M 1/36* (2006.01)
*A61B 17/11* (2006.01)

(52) U.S. Cl.
CPC ........... *A61B 17/11* (2013.01); *A61M 1/3655* (2013.01); *A61B 2017/1107* (2013.01); *A61B 2017/1139* (2013.01)

(58) Field of Classification Search
CPC ................. A61M 1/3655; A61B 17/11; A61B 2017/1139; A61B 2017/1135; A61B 2017/1107
See application file for complete search history.

(56) References Cited

U.S. PATENT DOCUMENTS

| | | | | |
|---|---|---|---|---|
| 2001/0044631 A1* | 11/2001 | Akin | ...................... | A61B 17/11 606/153 |
| 2004/0034377 A1* | 2/2004 | Sharkawy | .......... | A61B 17/0057 606/153 |
| 2004/0172049 A1* | 9/2004 | Lee | ......................... | A61B 17/11 606/153 |
| 2005/0080439 A1* | 4/2005 | Carson | ............... | A61B 17/0643 606/153 |
| 2006/0111733 A1* | 5/2006 | Shriver | ..................... | A61F 2/06 606/153 |
| 2006/0247605 A1* | 11/2006 | Edoga | ................. | A61M 1/3655 604/891.1 |
| 2008/0300528 A1* | 12/2008 | Cull | .......................... | A61F 2/06 604/6.16 |
| 2013/0041453 A1* | 2/2013 | Consigny | ............ | A61M 1/3655 623/1.15 |
| 2015/0119908 A1* | 4/2015 | Consigny | ............... | A61B 17/11 606/156 |

\* cited by examiner

*Primary Examiner* — Katrina M Stransky
(74) *Attorney, Agent, or Firm* — Brinks Gilson & Lione

(57) ABSTRACT

A multi-part medical implant device assembly for use in the surgical creation of an arteriovenous fistula is described herein, the implant device having an arterial section with an arterial lumen provided therein, a venous section with a venous lumen provided therein, and a connector section with a connecting lumen provided, the connector section serving to provide a fluid pathway from the arterial section to the venous section. The device may be formed of a top and a bottom portion, where the two-part assembly may facilitate surgical implantation.

20 Claims, 8 Drawing Sheets

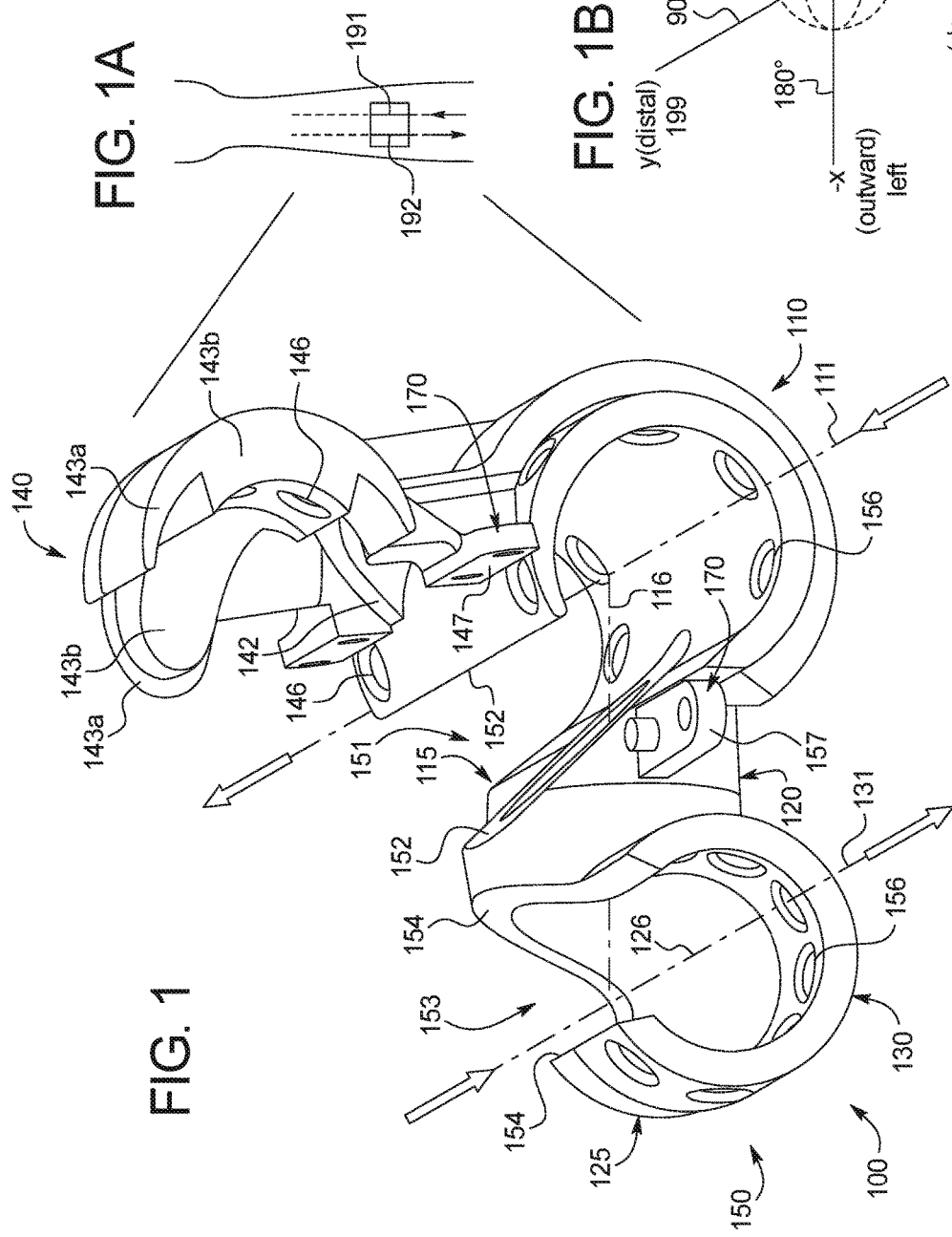
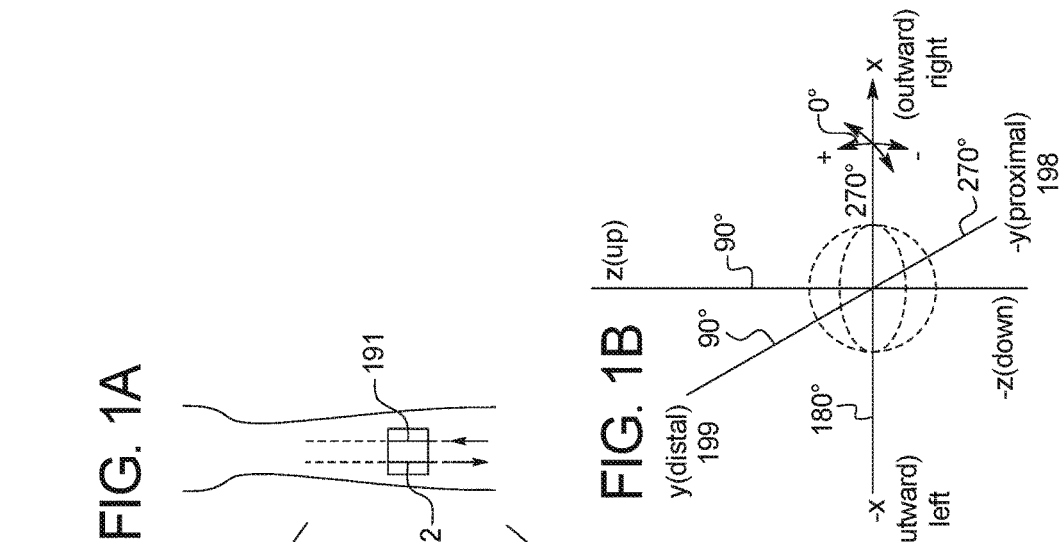

MEDICAL DEVICE AND CORRESPONDING METHOD OF USE FOR ARTERIOVENOUS FISTULA CREATION

TECHNICAL FIELD

This disclosure relates to a medical device for use in the creation of an arteriovenous fistula (AVF) and a surgical method for implanting the device into a patient.

BACKGROUND

Patients suffering from certain ailments, including end-stage renal disease (ESRD), may undergo hemodialysis treatment. Hemodialysis is a process in which arterial, or outward flowing, blood is removed from the body, filtered, and subsequently reintroduced as venous, or returning, blood. In order for the dialysis process to be efficiently carried out, a relatively high blood flow rate is required (approximately 600 ml/min).

While the vascular system is capable of providing these flow rates, safely accessing the vascular system can be problematic. For example, while a central venous catheter (CVC) may provide immediate access to the vascular system close to the heart at sufficiently high flow rates, it is associated with a high risk of infection due to permanent exposure to external environmental conditions through the entrance site. Accordingly, the use of a CVC is not a viable option for long term access to the vascular system for hemodialysis purposes.

Directly accessing, or cannulating, the artery is similarly not viable, as it generally requires inserting two needles directly into the artery (piercing the arterial wall) for each dialysis treatment. As patients may undergo dialysis 3-4 times a week, the repeated perforation of the arterial wall may ultimately lead to destruction of the artery through stenosis. Moreover, accessing the artery itself may cause heightened pain and discomfort to the patient. Cannulation of the artery may also be practically limited, in that arteries with sufficiently high flow rates are harder to find within the body and more difficult to access.

In order to facilitate repeated access, as required for treatment of ESRD by hemodialysis, surgeons have historically resorted to grafts to create a bridge between an artery and a vein, where the blood flowing in the artery may be diverted, in part, to flow through the graft and into the vein. The process effectively bypasses narrower, more distally located, capillaries to achieve the desired flow rates. Hemodialysis may then be performed through cannulation of the graft, as distinct from the artery itself.

While repeatedly accessing the graft is preferable to cannulating the artery, the graft too may deteriorate over time and may require subsequent intervention to repair or replace the graft. The material used to form the graft (e.g., ePTFE tubing), may also increase the likelihood of forming occlusions, or clots, on the inner lumen of the graft, as it places a foreign material (e.g., the entire length of ePTFE tubing, e.g., 30-45 mm) into contact with the blood stream. In this way, the graft may narrow over time and may be rendered unsuitable for use in hemodialysis, requiring further intervention (e.g., a balloon dilation or an additional graft).

The use of grafts is generally not a preferred method for vascular access, and surgeons often favor the surgical creation of an arteriovenous fistula. At a high level, the surgical process aims at attaching a vein directly to an artery, bypassing the distal capillaries to achieve the necessary flow rate. The surgical procedure typically begins by exposing the desired vessels, identifying and ligating a target vein and artery, to prevent blood flow into the surgical site. The vein, having a distal portion in the patients hand and a proximal portion towards the patient's heart, is completely transected, which may introduce stress due to the vasospasm of the transected vessel. The distal end of the proximal portion is secured prior to transection and is then bent towards the artery. The distal end may be splayed open slightly, and attached around a longitudinal incision made in the artery, thereby allowing for blood to flow from the artery into the vein once the artery is no longer ligated. The surgical procedure itself is quite delicate, and may be difficult to perform for even the most experienced surgeon.

In order to successfully form a fistula, the vein once transected and attached to the artery must undergo a maturation process in which the vein enlarges, or dilates, in order to accommodate the increased pressure and higher flow rates. While the fistula maturation process is poorly understood, the maturation process is driven by a positive feedback mechanism in which high flow rates and increased pressure lead to dilation of the vein, which in turn accommodates increased flow rates and pressure. As a specific example of the fistula maturation process, which may take 2 months or more, a 2.5 mm-3 mm vein having a flow rate of <30 ml/min may mature into a 6 mm vein, providing a flow rate of roughly 600 ml/min.

Once the fistula has formed, it may be cannulated, or accessed, for each hemodialysis treatment that is performed. While the fistula may ultimately deteriorate, the risk of stenosis is relatively lower, in part, because no foreign material (e.g., ePTFE tubing) is introduced into the system. Furthermore, clinical research has shown that patients with AVFs have better long-term patency rates and reduced incidence of required intervention relative to alternative methods. Research shows that AVFs have the longest survival, result in fewer access related procedures, fewer hospitalizations due to infection and lower overall costs of care.

Even so, the surgical creation and maturation of a fistula is only successful in roughly 50-80% of patients. While the reasons for failure are not clearly understood, the physical stress and technical difficulty of the surgery may play a significant role in its failure. The failure may, for example, be associated with vascular trauma or occlusion of blood flow during surgery, which may result in neointimal hyperplasia and thrombosis. As another example, tissue downstream of the anastomosis site that proliferates to heal may over proliferate, resulting in neointimal thickening. The procedure may also fail due to stenosis, which may be associated, in part, with the cutting of surrounding muscle and tissue to mobilize the vein or the manipulation of the vein by splaying its end for attachment to the artery. Moreover, because the vein often times may move more than 10 mm in the lateral direction, it may cause bending, and possible kinking, of the vein, which may result in a phenomenon referred to as "swing stenosis."

Also, as noted above, successful fistula maturation requires sufficient post-operative flow rates to promote vein dilation, but this may be impeded by trauma to the vein or artery or poor and inconsistent surgical technique. A primary cause of difficulty with the procedure is the vasospasm of the vein in response to ligation, which makes it much more difficult to correctly suture the vein to the artery. Additionally, while high post-operative flow rates support fistula maturation and vein dilation, they also introduce hemodynamic stresses, including the shear stress resulting from a turbulent flow and higher flow rate.

SUMMARY

A medical implant device is currently provided that may be used in the surgical creation of arteriovenous fistulas. The implant device includes an arterial section that may externally secure an artery, a venous section that may be inserted into, or externally secured to, a vein, and a connector section provided therebetween. The implant device may be formed from a top and a bottom portion that complement one another and join together to provide a fluid pathway within the arterial section, through the connector section and into the venous section.

BRIEF DESCRIPTIONS OF THE DRAWINGS

FIG. 1 illustrates a first embodiment of the medical implant device in an open state; FIG. 1A provides an illustration of a surgical site; and FIG. 1B provides a reference coordinate system.

DETAILED DESCRIPTION

The implantable device and surgical method described herein seek to address the limitations of traditional devices and surgical methods in creating an arteriovenous fistula, where the device may serve as a "jump graft" between arterial and venous blood vessels. For example, the device may limit exposure of the blood to foreign materials, particularly relative to grafts, and may help to avoid excessive mobilization of the vein and/or artery, including the lateral movement of the vein. To that end, the device may be formed of a biocompatible material (e.g., ePTFE) and may be available in different shapes and sizes to accommodate for different physical geometries and surgical conditions. Modern manufacturing capabilities (e.g., computer vision, rapid prototyping, 3D printing, printing with biological material, etc.) may also be used to allow for the creation of custom, patient specific, implant devices.

In some embodiments, the device may allow for the vessels to be secured to the device prior to ligation, which may significantly reduce the challenge and trauma associated with attaching the vessels, as the initial fixation may be performed prior to vasospasm. Furthermore, by securing the device prior to ligation, the duration of occlusion of the vessels during surgery may be significantly reduced. This may lessen the risk of failure due to thrombosis as well as reduce ischemic damage to the limb.

The device may be formed of several pieces, which interact with one another to form a single implant device. In some embodiments, for example, the device may comprise two separate pieces that may be assembled together. The device may include various features to help align and/or secure the pieces together. In other embodiments, the device may have two pieces that are slotted within each other, or hinged together, having an open and a closed position. In such embodiments, the device may include features that hold or retain the device in the open and/or closed positions.

The embodiments described below may illustrate various features that can be included in a medical implant device for use in the creation of an AVF. The structure and features of the implant device may also allow for an improved surgical procedure for creation of an arteriovenous fistula. While the figures illustrate embodiments suitable for a particular anatomical context, the invention is not so limited. The implant device may vary in form to account for anatomical differences between patients, which may further limit surgical trauma and promote better surgical outcomes.

First Embodiment

Figure 2:
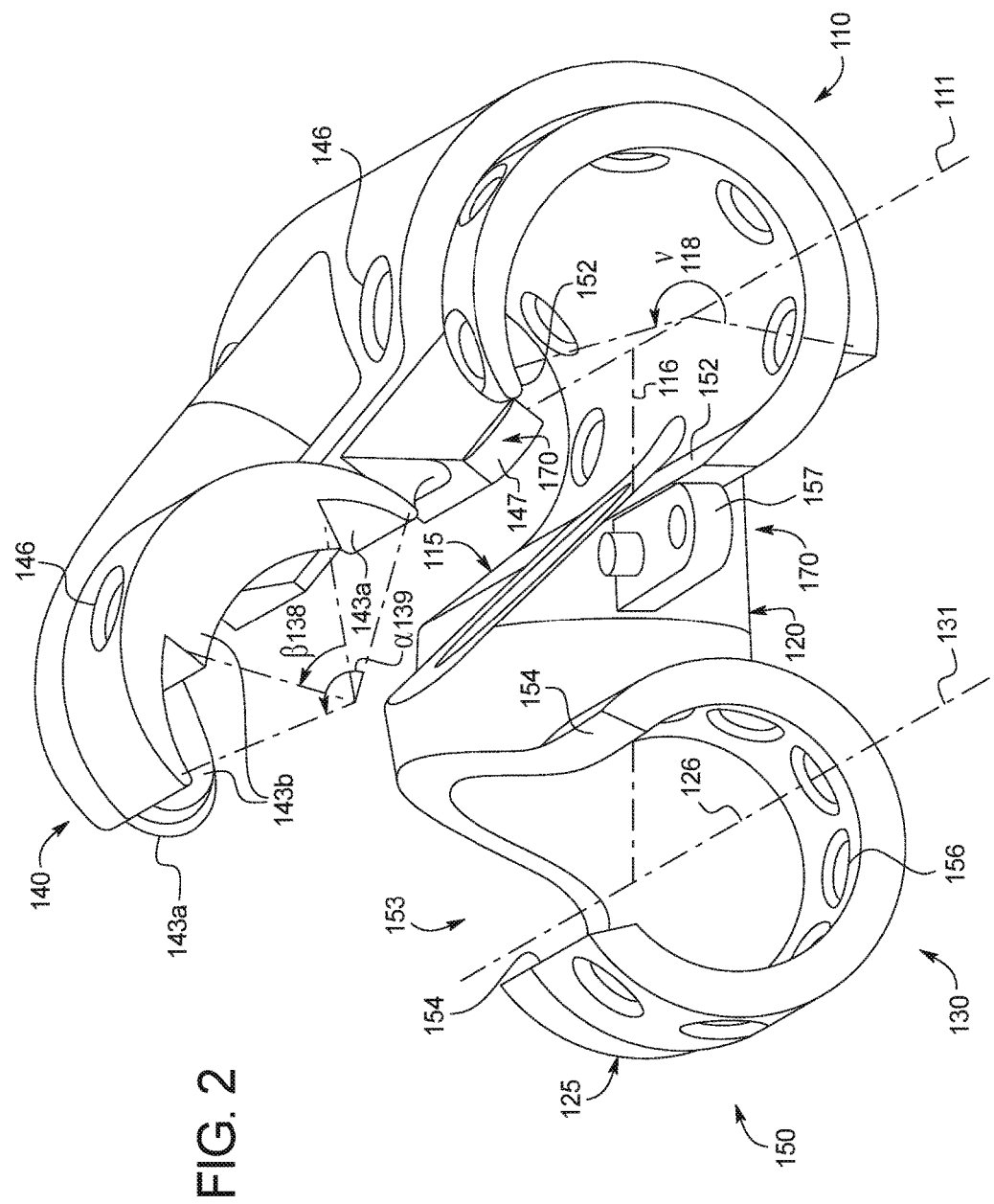
FIG. 2 illustrates the first embodiment of the medical implant device in a partially closed state.
Figure 3:
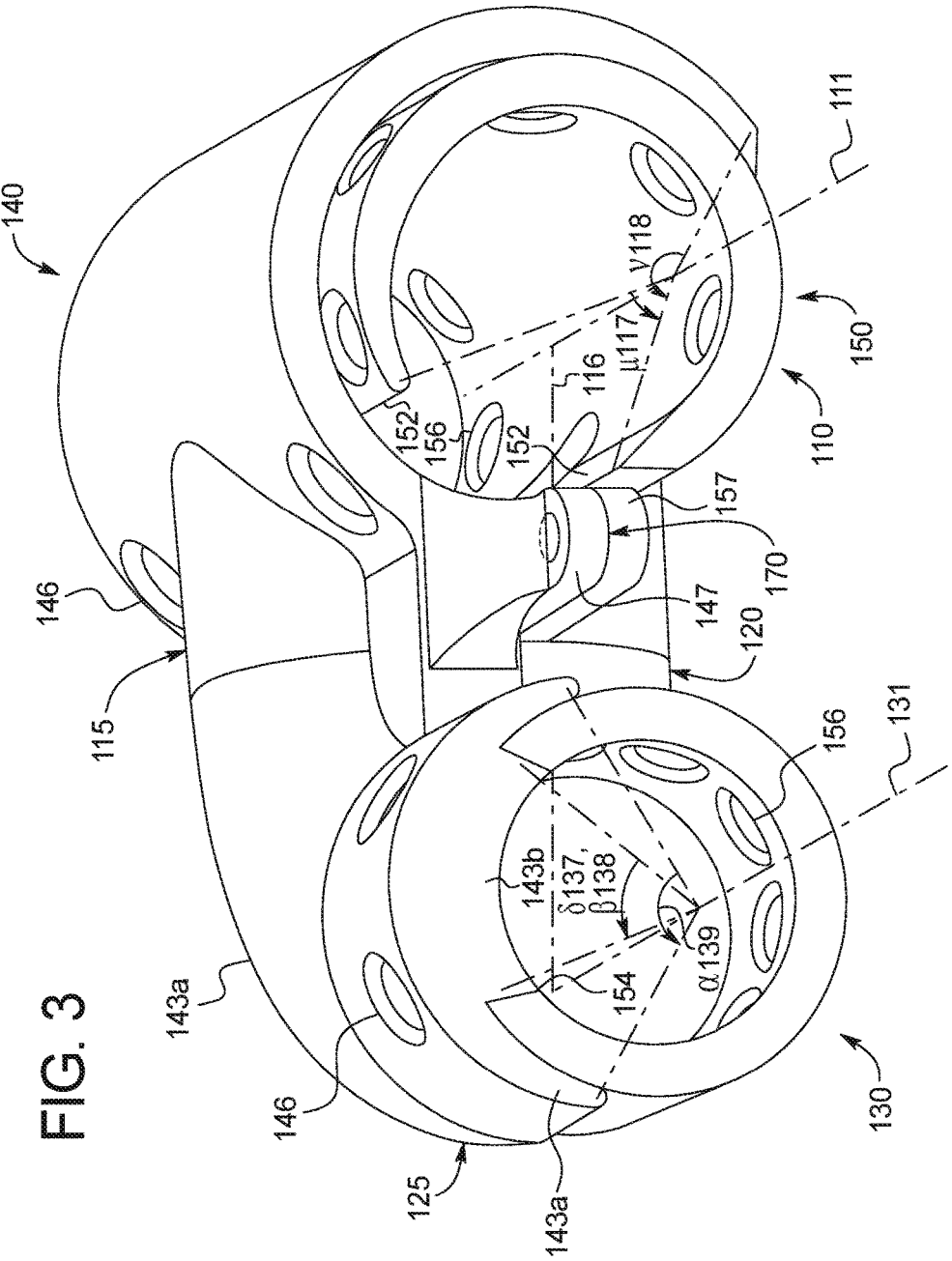
FIG. 3 illustrates the first embodiment of the medical implant device in a closed state.
Figure 4:
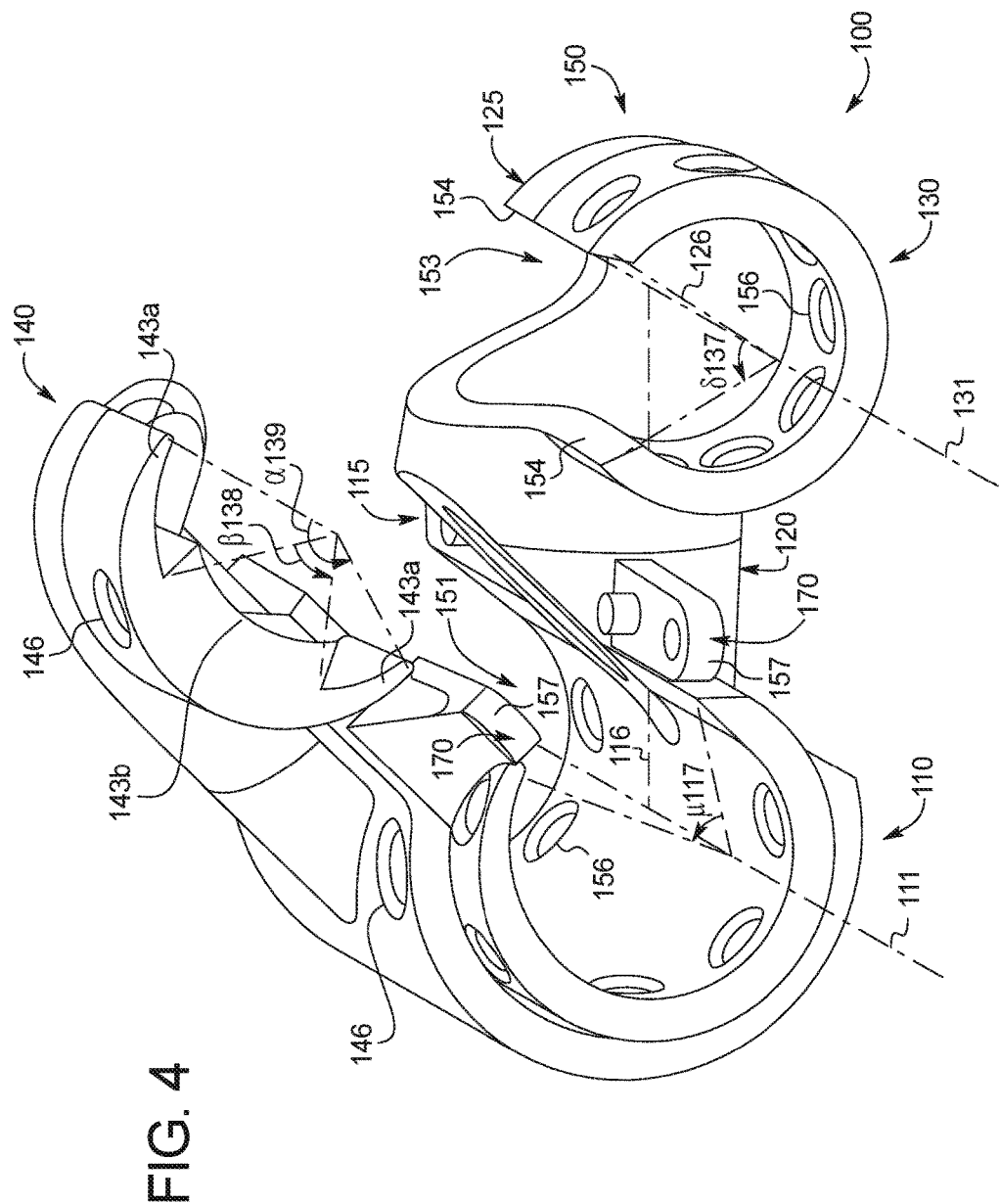
FIG. 4 illustrates the first embodiment of the medical implant device in a partially closed state.

FIGS. 1-4 illustrate different views of a first embodiment of the implant device 100. FIG. 1 illustrates the implant device in an open state, FIGS. 2 and 4 illustrate the implant device in a partially closed state, and FIG. 3 illustrates the implant device in a closed state. FIGS. 1-3 illustrate an implant device 100 generally suitable for use where the artery 191 is to the right of the vein 192, and FIG. 4 illustrates an implant device 100 that may be suitable for use where the artery 191 is to the left of the vein 192. The device of FIG. 4 is a mirror image of that shown in FIGS. 1-3 and both versions together may be viewed as one embodiment. FIG. 1A provides an illustration of the surgical site identifying the artery 191 and vein 192 and corresponding direction of arterial and venous blood flow. FIG. 1B illustrates a coordinate system that may be used to provide a common frame of reference for describing the implant device 100. As illustrated, FIG. 1B may define proximal 198 and distal ends 199 (along the y-axis), up and down directions (along the z-axis) and a laterally outward left and right direction (along the x-axis). FIG. 1B may also identify a positive and negative direction of rotation in the x-y and x-z planes.

The implant device 100 may have three different sections: an arterial section 110, a connector section 120 and a venous section 130. With reference to FIG. 3, which illustrates the implant device 100 in a closed or assembled state, the arterial section 110 may be oriented along an arterial axis 111, extending from a proximal end 198 of the implant device to a distal end 199 of the implant device, and having an overall length of 10-25 mm. The arterial section 110, as illustrated, may be generally tubular in form, having a roughly uniform inner diameter of 5-10 mm, and may provide an inner cavity in which the artery 191 may be situated.

The venous section 130 may be oriented along venous axis 131 and may extend from a proximal end of the implant device 198 towards a distal end 199 of the implant device, and have an overall length of 5-10 mm. The venous section 130 may also be generally tubular in form, having an inner diameter of 3-5 mm, and may be able to accommodate a vein 192 within its inner cavity. The arterial axis 111 and venous axis 131, as illustrated, may run parallel to one another and may be spaced apart in the lateral direction from one another so as to align with the artery 191 and vein 192 which may be similarly oriented.

The connector section 120 may extend between the arterial section 110 and venous section 130 and may be generally tubular in form, having an inner diameter of 4-9 mm. The connector section 120 may join the arterial section 110 at an arterial connection region 115, and may join the venous section 130 at a venous connection region 125. The connector section 120 may gradually transition from the arterial section 110 to the venous section 130. As illustrated, for example, the connector section 120 may have an overall elbow like shape, and may extend 3-5 mm laterally (along the x-axis) from the arterial section 110 and 3-5 mm longitudinally (along the y-axis) to the venous section 130 and sweep through an arc of 90 degrees. In this way, the connector section 120 may serve to provide a conduit through which arterial blood flowing in the distal direction may be redirected into the vein 192, flowing in the proximal direction.

As illustrated in FIG. 3, the connector section 120 may join the arterial section 110 at an arterial connection region 115 to form a generally T-shaped tubular junction at a position along the length of the arterial section 110. The connector section 120 may be shaped such that it is oriented along an arterial connection axis 116 where the connector section 120 joins the side region 115. The arterial connection axis 116 reflects the orientation of the connector section 120 as it joins the arterial section 110 at the side region 115. As illustrated, the arterial connection axis 116 is perpendicular to the arterial axis 111, thereby forming the T-shaped junction, but this may not necessarily be the case as the implant device may need to account for different anatomical variations between patients and surgical sites (as described in greater detail below). For instance, the connector section 120 may be generally U-shaped and may join the arterial section 110 at an angle to form a Y-shaped junction. The connector section 120 may also join the venous section 130 at the distal end of the venous section 130 at a venous connection region 125, where the connector section 120 may be oriented along a venous connection axis 126. The venous connection axis 126 reflects the orientation of the connector section 120 as it joins the venous section 120 at the venous connection region 125. As illustrated in FIG. 3, the venous axis 131 and venous connection axis 126 are coextensive with one another, but this is not necessarily the case as the implant device may need to account for different anatomical variations between patients and surgical sites (as described in greater detail below).

Multi-Piece Construction

As previously noted, the implant device 100 may be formed from one or more pieces that are joined together. As will be described in greater detail below, the multi-piece nature of the device may provide a surgical advantage, for example and without limitation, by allowing for initial securement of the implant device 100 to the artery 191 and/or vein 192 prior to ligation.

In FIGS. 1-4, for example, the implant device 100 may have both a top portion 140 and a bottom portion 150, which may be generally complimentary to one another and may join together to form the arterial section 110, the connector section 120, and the venous section 130. FIG. 1 illustrates the implant device 100 in an open configuration, where the complimentary features of the top and bottom portion 140, 150 may be seen. The description below is once again made with reference to the coordinate system in FIG. 1B.

Arterial Section

With reference to the arterial section 110, the bottom portion 150 may be generally tubular in shape with an arterial opening 151 through its wall and along its length (along arterial axis 111). The arterial opening 151 may allow access to the inner cavity of the arterial section 110. As illustrated in FIGS. 3 and 4, for example, the bottom portion 150 may be open through an angle of μ degrees 117 at a portion through its top. In the configuration illustrated in FIG. 3, the opening is generally provided in the upper left quadrant. More specifically, described with reference to the coordinate system in FIG. 1B, the opening may be provided in the bottom portion 150 from a first radial position at about +100 degrees to a second radial position at about +175 degrees, thereby providing an opening 151 with an overall opening of about 75 degrees. The size of the overall opening may vary, for example, ranging from about 50-80 degrees so as to accommodate arteries of different size. The position of the opening may similarly vary. As a practical matter, it may be desirable to access the bottom portion 150 from above (+180 to 0 degrees) so as to place the artery 191 into the bottom portion 150 during the surgical procedure. While not illustrated, it may also be the case that the opening 151 of the implant device may be provided in the upper right quadrant of the bottom portion 150, so as to allow for easier placement of the artery 191 during the surgical procedure. As another example, in FIG. 4, where the arterial 110 and venous sections 130 have been transposed, an opening of about 75 degrees is provided in the upper right quadrant from a first radial position at about +5 degrees to a second radial position of about +80 degrees.

The opening 151 may also result in exposed edges 152 along the bottom portion 150 along the length of the arterial section 110. The exposed edges 152 may be formed to be atraumatic (or reduce the potential for trauma), which may involve the bottom portion 150 being tapered, beveled or rounded along the exposed edges 152. With reference to FIG. 3, for example, the bottom portion 150 may be rounded along the edges 152 formed at the first radial position (about +100 degrees) and tapered along the edge formed at the second radial position (about +175 degrees). This may allow the artery 191 to be placed into the bottom portion 150 of the arterial section 110 through the arterial opening 151 with minimal trauma or damage to the external wall of the artery 191.

Venous Section

With reference to the venous section 130, the bottom portion 150 may be generally tubular in shape with a venous opening 153 through its wall along its length (along venous axis 131). The venous opening 153 may allow access to the inner cavity of the venous section 130. As illustrated in FIGS. 3 and 4, for example, the bottom portion 150 may be open through an angle of δ degrees 137 at a portion through its top. More specifically, described with reference to the coordinate system in FIG. 1B, the venous opening 153 may be provided in the bottom portion 150 from a first radial position at about +60 degrees to a second radial position at about +120 degrees, thereby providing an opening 153 centered about the vertical axis (z-axis) with an overall opening of about 60 degrees. The size of the overall opening may vary, for example, ranging from about 50-80 degrees so as to accommodate veins 192 of different size. The position of the opening may similarly vary, and need not be centered about the vertical axis. As a practical matter, however, it may be desirable to access the bottom portion 150 from above (+180 to 0 degrees) so as to place the vein 192 into the bottom portion 150 during the surgical procedure.

The venous opening 153 may also result in exposed edges 154 along the bottom portion 150 along the length of the venous section 130. The exposed edges 154 may be atraumatic (or reduce the potential for trauma), which may involve the bottom portion 150 being tapered, beveled or rounded along the exposed edges 154. With reference to FIG. 4, for example, the bottom portion 150 may be beveled along the edges 154 formed at the first radial position (about +60 degrees) and tapered along the edges 154 formed at the second radial position (about +120 degrees). This may allow the vein 192 to be placed into the bottom portion 150 of the venous section 130 through the venous opening 153 with minimal trauma or damage to the external wall of the vein 192.

The Connector Section

The arterial section 110 and venous section 130 may influence the shape of the bottom portion 150 of the connector section 120, specifically along the venous axis 131 and through the arterial connection region 115. The venous opening 153 provided in the venous section 130, for example, may extend into the venous connection region 125 along venous axis 131 and may be open through the same angle δ 137 in this region. As illustrated in FIG. 1 for example, the venous opening 153 may extend in the connector section 120, and may continue along venous connection axis 126 as the connector section 120 transitions towards the arterial connection axis 116. The bottom portion 150 of the connector section 120 may match the bevel or chamfer of the exposed edges 154 at a first radial position (about +60 degrees in FIGS. 1-3, and about +120 degrees in FIG. 4) as the venous opening 153 extends into connector section 120 along the venous axis 131. The bottom portion 150 may also provide atraumatic edges 154 (or edges 154 that reduce the potential for trauma) through the opening 153 in the venous connection region 125. This may allow the vein 192 to be placed into the extended opening 153 of the bottom portion 150, which may then slide into place in the bottom portion 150 of the venous section 130, with minimal trauma or damage.

In a similar way, the arterial opening 151 provided in the arterial section 110 may extend into the arterial connection region 115. As illustrated, for example, the top 140 and bottom portion 150 of the connector section 120 may be split or divided along the second radial position (about +175 degrees in FIGS. 1-3 or about +5 degrees in FIG. 4) and may match the bevel or chamfer of the exposed edges 152. The atraumatic edges 152 (or edges 152 that reduce the potential for trauma) may also be provided through the connector section 120 of the bottom portion 150. This may allow the artery 191 to be placed in the extended opening 151 in the bottom portion 150 of the connector section 120, which may then slide into place in the bottom portion 150 of the arterial section 110, with minimal trauma or damage.

Complimentary Top and Bottom Portions

The top portion 140 may be complimentary to the bottom portion 150, and the top and bottom portions 140, 150 may be assembled to form the implant device 100. As illustrated, the top and bottom portions 140, 150 may be shaped so as to form a sealed relationship in the venous section 130 and through the connector section 120, while forming a generally closed relationship in the arterial section 110. The implant device 100 may be assembled to provide a fluid pathway between the arterial section 110, through the connector section 120, and into the venous section 130, through which blood may flow. The top and bottom portion 140, 150 may remain in the closed position by having sufficiently tight tolerances between the top and bottom portion 140, 150 to form a snap fit. Additionally, or in the alternative, the implant device 100 may be provided with securing portions 170 (described in greater detail below), which may clasp or otherwise positively secure the top and bottom portions 140, 150 together.

As illustrated, for example, the top portion 140 may be shaped so as to join venous opening 153 through the venous section 130 and connector section 120. As illustrated in FIG. 3, where the cross section of the venous section 130 is shown, the top portion 140 may be shaped to pass through an arc of α 139 (identified in FIGS. 2-4), and having a protruded region 143b, through a sub-arc β 138 (identified in FIGS. 2-4) with a surrounding tapered region 143a. The protruded region 143b may be shaped to provide a seamless inner cavity when the top portion 140 joins the bottom portion 150, for example, the protruded region 143b may match venous opening 153 (e.g., sub-arc β 138 may match venous opening angle δ 137). For example, the protruded region 143b may extend from between about 50 degrees and about 80 degrees. The protruded region 143b may further match the bevel or chamfer of the venous opening 153. The surrounding tapered region 143a may extend beyond the venous opening 153 spanning between about 100-160 degrees (a first radial position of about +10 degrees and a second radial position of about +170 degrees). The tapered region 143a may be larger than the outer diameter of the bottom portion 150, and along with the protruded region 143b may interface with the bottom portion to form a seal through venous section 130.

The protruded region 143b may continue and extend into the connector section 120. As illustrated in FIG. 1, the protruded region 143b may maintain its shape through the venous connection region 125 and extend along the venous axis 131 as the connector section 120 transitions to the arterial connection axis 116. The tapered region 143a present in the venous section 130 may extend in the same, or similar, form through the connector section 120 as well, and may likewise provide a seal between the top and the bottom portions 140,150 through the connector section 120.

In the arterial section 110, the top portion 140 may be generally tubular in form having a larger diameter than the bottom portion 150. The top portion 140 may have an opening provided through its wall, such that the top and bottom portions 140,150 may interface with one another to form the closed arterial section 110 shown in FIG. 3. The top portion 140 may have a diameter slightly larger than that of the bottom portion 150 and may move between a fully open position, illustrated in FIG. 1, through a partially closed position FIG. 2, and into a fully closed position FIG. 3, where the arterial opening 151 (not illustrated in FIG. 3) in the bottom portion 150 is closed. As illustrated in FIGS. 1-3, the arterial section 110 of the top portion 140, having a larger diameter than the bottom portion 150, may be rotated about the bottom portion 150, from the open to the closed position. With reference to FIG. 2, illustrating the implant device in a partially closed position, the top portion 140 may pass through an angle of ν degrees 118 (also seen in FIG. 3). As the opening may generally vary from about 50-80 degrees, the top portion 140 may similarly need to span through an angle ν 118 slightly larger than the opening 151 (i.e., 51-81 degrees). The top portion 140 may have an arc length larger than the size of the opening 151 (e.g., spanning through about 150-200 degrees) in the bottom portion 150 and may be aligned to provide closure to the opening 151 when the implant device 100 is fully assembled. Accordingly, the top portion 140 of the arterial section 110 may extend from a radial position just beyond that of the first position of the opening 151 (greater than about +175 degrees), to within the second position of the opening 151 (less than about +100 degrees), ending at a radial position of about −35 degrees. By extending the top portion 140 beyond the second position (at about +100 degrees), better rotation and enhanced securement of the top portion 140 about and to the bottom portion 150 may be provided. The top portion 140 of the connector section 120 may also complement the bottom portion 150, so that it may form a seal through the arterial connection region 115 when in the closed position. The top portion 140 may, for example, provide a protruded region 142 (partially visible in FIG. 1) that compliments the bottom portion 150 in the arterial connection region 115, and forms a seamless inner cavity through the connector section 120.

Securing the Implant Device During Surgery

The implant device 100 may include various fixation features to help secure the top and bottom portions 140,150 together. As illustrated in FIGS. 1-4 for example, the implant device 100 may include a securing portion 170 that extends in the proximal direction from the connector section 120 and a securing portion 170 that extends in the distal direction from the connector section 120. The securing portions 170 may each have a top portion 147 and a bottom portion 157 which may interface with each other. As illustrated in FIG. 1, the top portion 147 may have a cavity that may correspond to a cylindrical extension provided in the bottom portion 157. This may help to align and secure the top and bottom portions 147,157 together, for example, through a friction fit or the use of an adhesive, epoxy or the like.

The implant device 100 may also have one or more fixation features 146, 156 at the proximal end of the arterial and venous sections 110,130 and at the distal end of the arterial section 110, which may allow for securement of the artery 191 and vein 192. As illustrated for example, the implant device 100 may have one or more holes 146, 156. The holes 146, 156 may be radially positioned about the proximal and distal ends of the arterial and venous sections 110,130, and may be uniformly spaced (e.g., every 15 degrees) or positioned at particular locations. In the arterial section 110, for example, the bottom portion may have uniformly spaced holes 156, while the top portion may have holes 146 at particular locations. In the venous section 130, the holes 146, 156 may be uniformly spaced (e.g., every 15 degrees) about its circumference.

The holes 146, 156 may be used to secure the vein 192 to the implant device using sutures, but in the case of the artery 191 sutures may be unnecessary and in such cases the implant device 100 may be sufficiently secured by the implant device itself, which may be enhanced through natural tissue growth into the holes 146, 156. In other embodiments, the implant device 100 may provide for a series of barbs along the inner surface of the proximal and/or distal portions of the arterial and venous sections 110,130. Such barbs, for example, may be provided in place of the illustrated holes on the top and bottom arterial portions 140,150, and may be 0.005 mm in size so as to secure the artery 191 with minimal damage to its external wall.

In yet other embodiments, the implant device 100 may provide a mesh or a cuff, for example, made of Dacron, a fabric, or other biocompatible material, which may be secured to the top and bottom portion 140,150 of the arterial and venous section 110,130 ends. The cuff may have a portion being secured to the implant device 100 and a portion being free to surround the artery 191 or vein 192. The cuff may be attached to the implant device 100 using an adhesive, epoxy, glue or the like, and in such cases the above described holes 146, 156 may provide a cavity that the adhesive may occupy to provide a better bond. The free portion of the cuff or mesh may be secured to the artery or vein using a suture that is interwoven into the cuff or mesh (i.e., a "purse string" suture).

Accounting for Anatomical Variations

As noted earlier, the size and shape of the implant device 100 may be varied to account for anatomical variations between patients while also promoting a successful surgical outcome (e.g., provide the flow rate necessary to promote fistula maturation and to achieve a target flow rate).

With reference to the figures, FIGS. 1-3 illustrate an implant device 100 suitable for use where the arterial section 110 is positioned laterally to the right of the venous section 130, and that of FIG. 4 for use where the arterial section 110 is positioned laterally to the left of the venous section 130. In FIGS. 1-3, the connector section 120 adjoins the arterial section 110 on its left side, whereas in FIG. 4, the connector section 120 adjoins the arterial section 110 on its right side. Furthermore, the connector section 120 in FIG. 4 has an elbow shape that transitions to the left, whereas the connector sections 120 in FIGS. 1-3 transition to the right.

As another example, the shape of the connector section 120 may be optimized so as to minimize turbulence, and concomitant hemodynamic stress, that may be introduced when changing the direction of blood flow. For example, the connector section 120 may take on a U shaped form, initially moving in the distal direction, where the arterial connection axis 116 may intersect the arterial axis at a shallow angle, for example, between about 10-30 degrees (e.g., arterial axis is aligned with the y-axis at about +90 degrees and the arterial connection axis is positioned between about +120 degrees and about +100 degrees). The connector section 120 may then gradually transition to the venous section 130, where the venous connection axis 126 is coextensive with venous axis 131. In so doing, the connector section 120 may pass through an arc of about 160 degrees, while passing through a net longitudinal distance of 3-5 mm in the proximal direction.

Variations in the size and configuration of the implant device 100 may not only promote more effective surgical procedures, but may also increase the number of possible AVF sites or locations. By accounting for different physical conditions within the body, previously unsuitable locations may become viable, if not ideal, target locations. For example, vessels that are easily accessible may also be separated by a relatively large distance, for which traditional surgical procedures may be poorly suited, for example, due to the relatively high risk of swing stenosis. By using the medical implant device 100 such locations may become suitable for fistula formation because the connector section 120 may account for all or part of the offset (lateral, longitudinal and vertical) between the artery 191 and vein 192.

As noted above, the arterial section 110 and venous section 130 may be laterally offset from one another, so as to account for the physical separation of the artery 191 and vein 192 within the body. In various embodiments, the connector section 120 may be able to account for a lateral offset of between 10-40 mm when transitioning between the arterial axis 111 and the venous axis 131. As the distance between the artery 191 and vein 192 may vary from patient to patient, the size and shape of the connector section 120 may be adjusted in order to account for different lateral offsets.

In some surgical contexts, it may be beneficial for the implant device 100 to account for longitudinal offsets between the arterial section 110 and the venous section 130, and the connector section 120 may be adjusted to account for this relative offset. For example, the connector section 120 may account for a longitudinal offset of 3-5 mm, adjoining the arterial section 110, at a region 10-15 mm from the proximal end of the device, and abutting the venous section 130 at its distal end, which may be 3-5 mm from the proximal end of the device. In other embodiments, the connector section 120 may be able to account for a longitudinal offset of 10-40 mm. Additionally, while the connector section 120, as illustrated, adjoins the arterial section 110 at its center along its length, the implant device is not thus limited and the connector section 120 may join the arterial section 110 at a more proximal or distal location along its length. Also, while not illustrated in the figures, the implant device may also account for a vertical offset between an artery 191 and vein 192, and in such cases, the connector section 120 may take on a helical shape, transitioning through the vertical offset while passing through an arc, to connect the arterial and venous sections 110,130.

As illustrated, the implant device 100 may be generally oriented in a single plane, and have an arterial and venous axis 111,131 that are parallel to one another and an arterial connection axis 116 that is perpendicular to both. While the artery 191 and vein 192 may generally run parallel to one another, as noted above, the orientation of the artery 191 and vein 192 may vary from one location in the body to another. Accordingly, the implant device 100 may be formed so as to accommodate different arterial 191 and venous 192 orientations.

Because surgical conditions and anatomical differences may vary from procedure to procedure and patient to patient, the configuration of the implant device 100 may similarly vary. The artery 191 and vein 192 may not run parallel to one another, as these blood vessels often travel circuitous paths having different relative orientations (e.g., non-parallel) in a particular region. For example, the artery 191 or vein 192 may be independently rotated in the x-y and y-z plane or have a vertical offset, in addition to the lateral and longitudinal offset previously discussed. With reference to the coordinate system of FIG. 1B, for example, the arterial axis 111, and consequently the arterial section 110, may be rotated in the x-y plane (e.g., having a radial direction between about +110 and +70 degrees) and in the y-z plane (e.g., having a radial direction between about +100 and +80 degrees). The venous section 130 and the venous axis 131 may likewise be rotated in the x-y plane (e.g., having a radial direction between about +110 and +70 degrees) and in the y-z plane (having a radial direction between about +110 and +80 degrees). The rotation of the arterial axis 111 and the venous axis 131 may notably be independent of one another, resulting in non-parallel arterial and venous sections 110, 130 that may converge or diverge. However, anatomical variation may practically limit the relative angular difference to between about 5-25 degrees.

In such cases, the shape of the connector section 120 in the arterial connection region 115 and venous connection region 125 may correspondingly be varied, for example, by varying the angle of intersection between the connection axis 116,126 and the arterial and venous axis 111,131 and/or by adjusting the arc through which the connector section 120 may sweep. In a first example, where the arterial axis 111 is rotated to a position of about +70 degrees in the x-y plane the arterial connection axis 116 may intersect the arterial axis 111 at an angle of about 70 degrees, while the connector section 120 may still sweep through a 90 degree arc in the x-y plane. In such cases, the arterial connection region 115 of the implant device 100 may better align with the direction of arterial blood flow, potentially reducing the intensity of the hemodynamic stress. As a second example, if the venous axis 131 is rotated to a position of about +75 degrees in the x-y plane, the connector section 120 may sweep through an angle of 75 degrees in the x-y plane such that the venous connection axis 126 remains coextensive with the venous axis 131. In cases where the venous axis 131 is rotated in the y-z plane, for example, to a position of about +100 degrees, the venous connection axis 126 and the venous axis 131 may no longer be coextensive and the connector section 120 may be curved accordingly in the venous connection region 125.

Surgical Implantation of the Device

The design of the implant device 100 may also facilitate surgery and promote long term success and fistula maturation. The surgical process may vary depending on the desired location (e.g., radiocephalic, brachiocephalic, brachiobasilic) and the corresponding shape and size of the implant device 100 that is used. It may be possible to identify potential surgical sites prior to surgical intervention based on medical imaging (e.g., x-ray/MRI) of the area. The surgeon may identify one or more target locations that he may assess during surgery to determine the ideal location. The target surgical site may be identified such that the expected surgical trauma is minimized. The surgery may begin by opening the surgical site and identifying the artery 191 and vein 192 most suitable for the procedure, for example, based on their size and/or accessibility. The surgeon may also select an appropriately sized and shaped implant device 100 to be used in the procedure.

The surgeon may first introduce the bottom portion 150 of the device into the patient, placing the artery 191 within the bottom portion 150 through the arterial opening 151. The surgeon may similarly place the vein 192 into the bottom portion 150 through the venous opening 153. As noted above, the bottom portion 150 may facilitate insertion of the artery and vein by providing a sloped surface that may reduce the potential for trauma in the arterial and venous connection regions 115, 125 of the connector section 120 that may help guide the artery and vein into the respective arterial and venous openings 151,153. It should also be noted that the implant device 100 may be positioned prior to ligation of the artery 191 or vein 192. If the implant device 100 is unsuitable, for example, for being improperly sized, the surgeon may be able to make this determination in advance of any trauma to the vein 192 or artery 191 (e.g., ligation, incision or transection).

With a suitable implant device 100 chosen, the surgery may proceed. With regard to the artery 191, the surgeon may ligate the artery and secure the artery to the bottom portion 150 using the holes 156 provided along the proximal and distal ends. As noted above, it may not be necessary to secure the artery to the implant device with sutures, for example, where the surrounding tissue provides a pocket in which the implant device 100 may securely rest, or where the artery 191 may be secured by barbs along the inner surface of the arterial section 110. In such cases, the surgeon may delay ligating the artery and may allow the artery 191 to naturally remain within the bottom portion 150 of the arterial section 110. In embodiments where a cuff is provided, the surgeon may place the cuff around the artery 191. The surgeon may ligate the vein 192 and may secure the vein 192 to the bottom portion 150 of the venous section 130, for example using a suture passing through holes 156 on the proximal portion of the bottom portion 150. Once the vein 192 has been secured, the surgeon may transect the vein 192 releasing the distal portion of the vein 192, with the proximal portion remaining attached to the implant device 100.

The surgeon may then ligate the artery, if not done so already, and may create a longitudinal incision along the arterial wall, near the arterial connection region 115, such that arterial blood may flow into the connector section 120. The surgeon may then place the top portion 140 around the bottom portion 150, if not done so already, and may swing the top portion 140 into the closed position. The surgeon may then secure the vein 192 and/or artery 191 through the holes 146 in the top portion 140. In embodiments where a cuff is provided, the surgeon may secure the cuff at each end using a "purse string" suture.

With the top portion 140 in place, the surgeon may allow blood flow to resume through the artery 191 and allow blood to return through vein 192 in the proximal direction. In embodiments where the arterial section 110 may not itself be sealed around the artery 191, the cuffs, when cinched, may promote clotting at the proximal and distal ends of the device 100. This clotting may result in the formation of a natural seal around the artery 191. The use of a cuff may also allow the surgeon to use an implant device 100 with a slightly oversized arterial or venous section 110,130. Despite being oversized, the cuff may allow the surgeon to achieve a seal between the implant device 100 and artery 191, and by being oversized the implant device may facilitate easier placement of the artery 191 within the bottom portion 150 of the arterial section 110 (i.e., by providing a larger arterial opening 151).

Additional Embodiments

FIGS. 5-8 illustrate additional embodiments of the implant device, having similar size, shape, form and features as the implant device described above. In these embodiments, for example, the implant devices may all be thought of as having an arterial section, a connector section and a venous section that are generally tubular in form and similarly oriented. The embodiments in FIGS. 5-8 may also be varied like the first embodiment described above in order to accommodate different anatomical and surgical conditions. The following description of the alternative embodiments may thus focus on the relative differences between the different embodiments.

Second Embodiment

Figure 5:
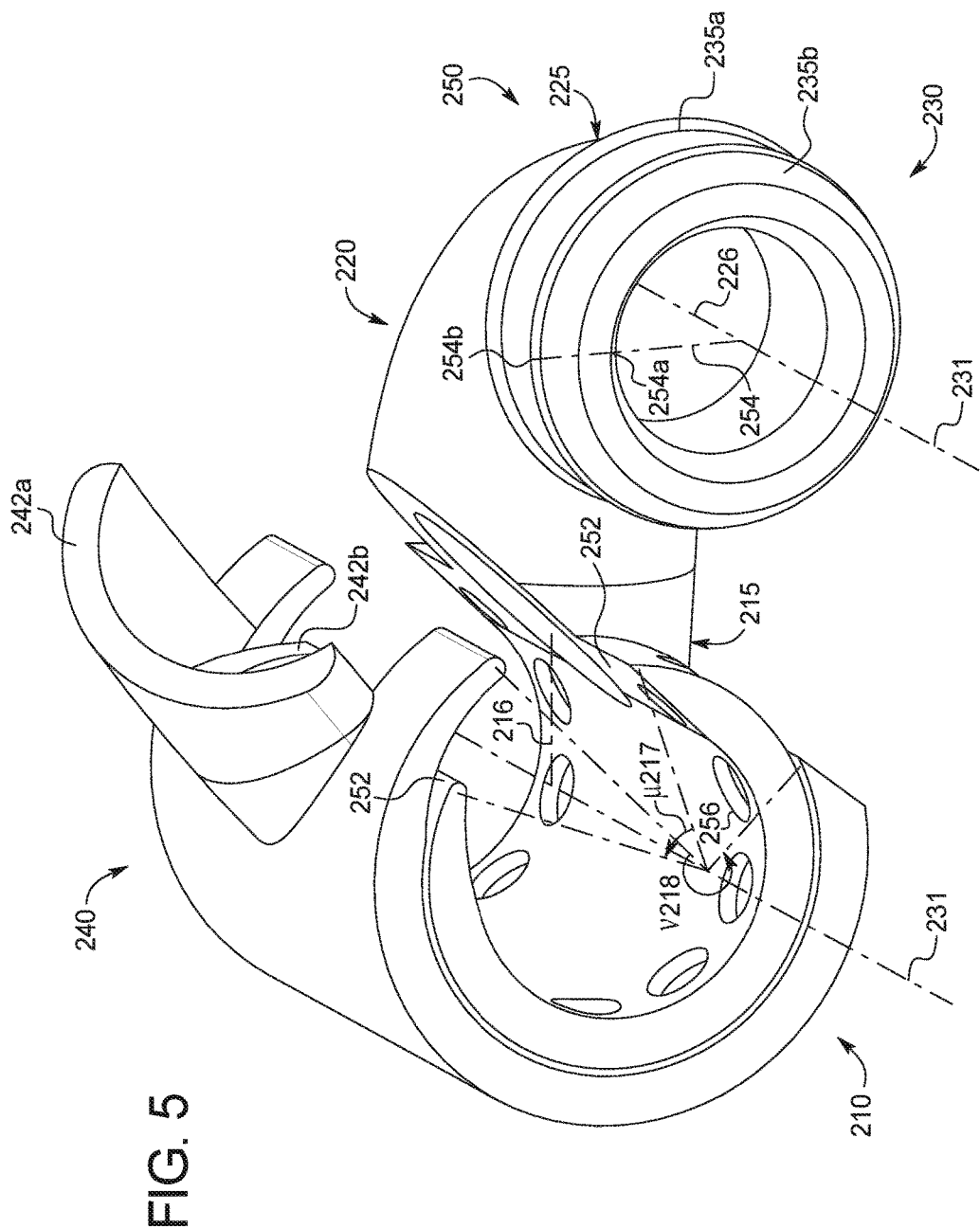
FIG. 5 illustrates a second embodiment of the medical implant device in a partially closed state.

FIG. 5 illustrates a second embodiment of the implant device 200, in a partially closed position. Like the first embodiment, the implant device 200 may generally be thought of has having three different sections, an arterial section 210, a connector section 220, and a venous section 230. Also like the first embodiment, the implant device 200 may have top and bottom portions 240, 250, where the top portion 240 fits to the bottom portion 250 to provide a hinge between an open and closed position.

The arterial section 210 is formed through the complement of top and bottom portions 240,250, the bottom portion 250 having an arterial opening 251, which may be open through an angle µ217, which may be varied in size and positions as described for the first embodiment. The arterial section 210 may similarly be provided with atraumatic edges 252 (or edges 252 that reduce the potential for trauma) along the perimeter of the opening 251. As illustrated, for example, the bottom portion 250 of the arterial section 210 may be open through about 40 degrees, from a first radial position of about +20 degrees to a second radial position at about +60 degrees, and having beveled or chamfered edges 252 and rounded edges 252 at about +20 and +60 degrees, respectively. The top portion 240, being slightly larger than the bottom portion 250, may rotate about the bottom portion 250 over arterial opening 251 when moving into the closed position, where it may also secure the top portion 240 to the bottom portion 250. The corresponding top portion 240, for example, may pass through an angle v 218 and may secure the top portion 240 and close the opening 251 in the bottom portion 250. In its closed position, for example, the top portion 240 may span roughly 240 degrees from a first position at about +20 degrees through a second position at about +260 degrees, having rounded edges 252 and beveled or chamfered edges 252 at each respective position.

Also, like the first embodiment, the shape of the arterial opening 251 may influence the shape of the connector section 220 through the arterial connection region 215. While not clearly depicted, the top portion 240 of the connector section 220 may be provided with a complementary portion 242b that complements the bottom portion 250 in the arterial connection region 215. In this way, the top and bottom portions 240,250 may assemble to form a sealed connector section 220. The top portion 240 may also provide a surrounding portion 242a that encompasses the bottom portion 250 in the arterial connection region 215. The surrounding portion 242a as illustrated may have a slightly larger (0.05-0.10 mm larger) diameter the bottom portion 250 through the connector section 220. The surrounding portion 242a may span between about 60-150 degrees about the arterial connection axis 216 (in the y-z plane). For example, as illustrated, the surrounding portion 242a spans about 90 degrees from a first radial position of about +135 degrees (relative to the y-axis at 0 degrees with the counter clockwise direction as positive) to a second radial position of about +45 degrees. The surrounding portion 242a may provide a clasping function, securing the top portion 240 to the bottom portion 250 in that region 215, by being appropriately toleranced with the connector section 220 in the arterial connection region 215 to form a friction fit.

As distinct from the first embodiment, much of the connector section 220 and the entire venous section 230 may be entirely formed as part of the bottom portion 250. The connector section 220 may, however, still generally serve to provide a conduit between the arterial section 210 and venous section 230. The venous section 230 may be an extension or continuation of the connector section 220, and provide one continuous lumen through both sections. The venous section 230 may be 3-5 mm in length. Also, in contrast to the first embodiment, the outer surface of the venous section 230 may have one or more ribs 235, around which a vein may be secured. As illustrated in FIG. 5, the venous section 230 has two identical ribs 235a, 235b having an outer diameter of between 8-13 mm, spaced along the length of the venous section 230 (e.g., at 1-2 mm offsets).

Differences in the Surgical Procedure

The differences described above, between the first and second embodiments, may also result in modifications as to how the surgical procedure is performed. Preparation for the procedure may be similar, involving the pre-identification of target surgical sites, and the procedure may begin in similar fashion, by exposing the surgical site and identifying the artery 291 and vein 292 most suitable for the procedure.

With the appropriate implant device 200 chosen (e.g., the implant device best suited for the particular arterial and venous orientation), the surgeon may ligate the vein 192, restricting blood flow into the surgical site, and make an incision (e.g., plus sign, longitudinal, etc.) in the venous wall such that the venous section 230 of the implant device 200 may be inserted into the vein 292. The surgeon may then secure the vein 292 about the venous section 230 of the implant device 200, for example, by using a "purse string" suture, woven through the vein 292.

The surgeon may also ligate the artery 291, slide the artery 291 into the arterial section 210, and make an incision along its length such that blood will pass into the arterial connection region 215 once blood flow is resumed. The surgeon may also choose to secure the artery 291 to the implant device using sutures and suture holes 256. As noted above, it is not always necessary to secure the artery to the implant device, for example, where the surrounding tissue provides a pocket in which the device 200 may securely rest. In such cases, the surgeon may elect to not secure the artery 291 to the arterial section 210, avoiding any unnecessary perforations of the arterial wall. Such methods may also be unnecessary in embodiments where the bottom portion 250 is provided with barbs 260. Furthermore, where a cuff or mesh is provided, securing the device by cinching the cuff 260 about the artery 291 may suffice to secure the implant device 200 about the artery 291.

With the artery 291 and vein 292 in place, the surgeon may place the top portion 240 in place and rotate it into the closed position, which may further secure the artery 291 within the arterial section 210. The surgeon may then transect the vein 292 such that the distal portion is released, with the proximal portion remaining secured to the implant device 200 at venous section 230. The surgeon may notably choose to transect the vein at any point after it has been secured to the implant device 200, and by doing so minimizes the effect that any resultant vasospasm may have.

A Third Embodiment

Figure 6:
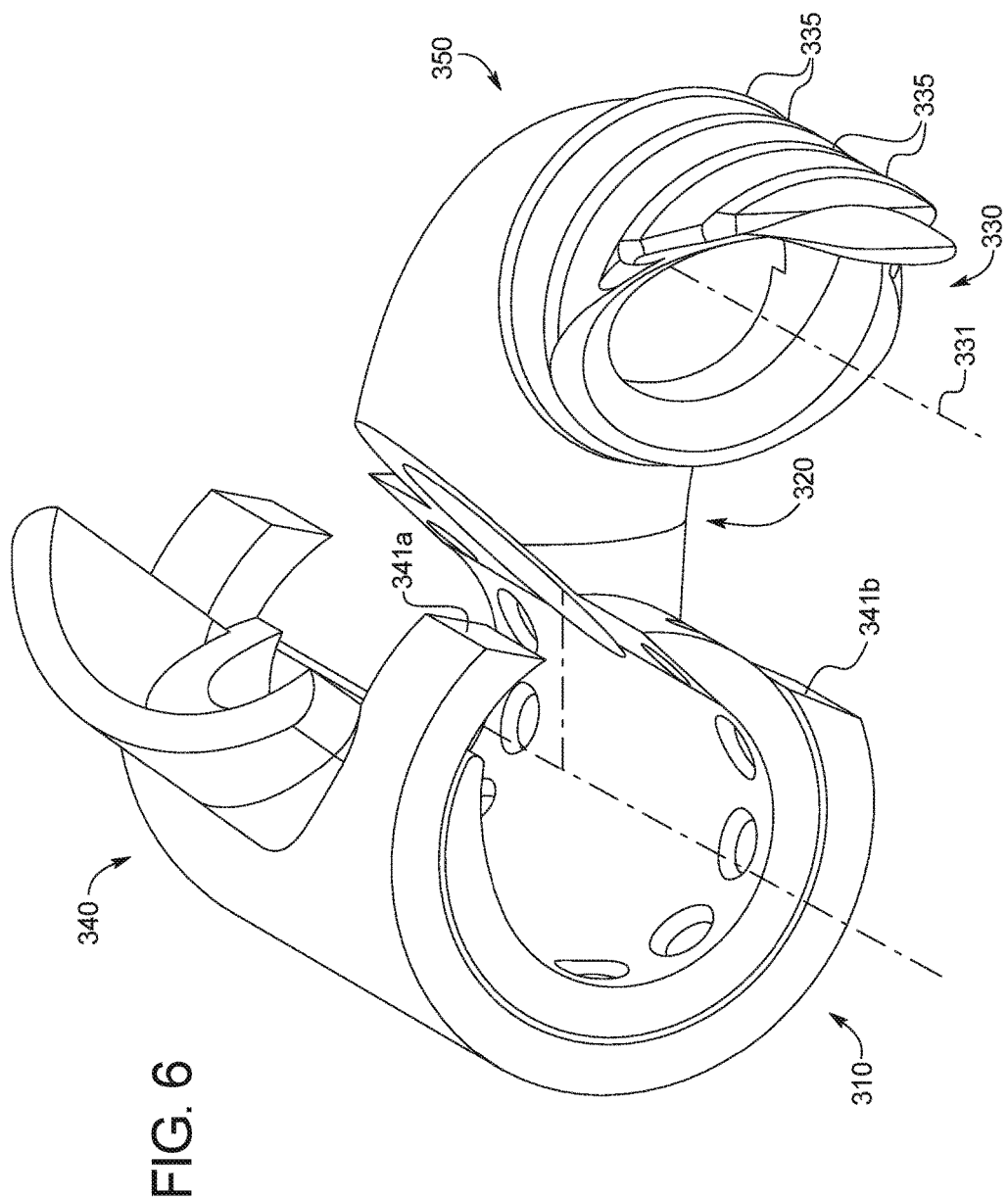
FIG. 6 illustrates a third embodiment of the medical implant device in a partially closed state.

A third embodiment is illustrated in FIG. 6, which shows an implant device 300 that is similar to, and in many respects the same as, the second embodiment just described. Like the second embodiment, the implant device 300 may generally be thought of has having three different sections, an arterial section 310, a connector section 320, and a venous section 330. Also like the second embodiment, the implant device 300 may have top and bottom portions 340, 350, where the top portion 340 fits to the bottom portion 350 to provide a hinge between an open and closed position. The arterial section 310 and connector section 320 are the same as the second embodiment except that the top portion 340, as illustrated, may have a uniform chamfer or bevel along both of its sides 341a, 341b.

The venous section 330 is notably distinct from that of the first and second embodiment, having a unique shape extending along venous axis 331. As illustrated, for example, the venous section 330 may have a fingernail like shape, with an annular cross section at its distal end that rapidly tapers towards the laterally outward portion of the venous section 330 ending at a point at its proximal end. The venous section 330, like that of the second embodiment, may have ribs 335, for example, having an outer diameter of 8-13 mm and being uniformly spaced (every 1-2 mm) along its length.

Differences in the Surgical Procedure

The design of the venous section 330, as illustrated in FIG. 3, may also affect the surgical procedure that is performed. In particular, the shape of the venous section 330 may facilitate easier insertion into the vein 392, and may require a smaller incision to be made in the venous wall.

A Fourth and Fifth Embodiment

Figure 7:
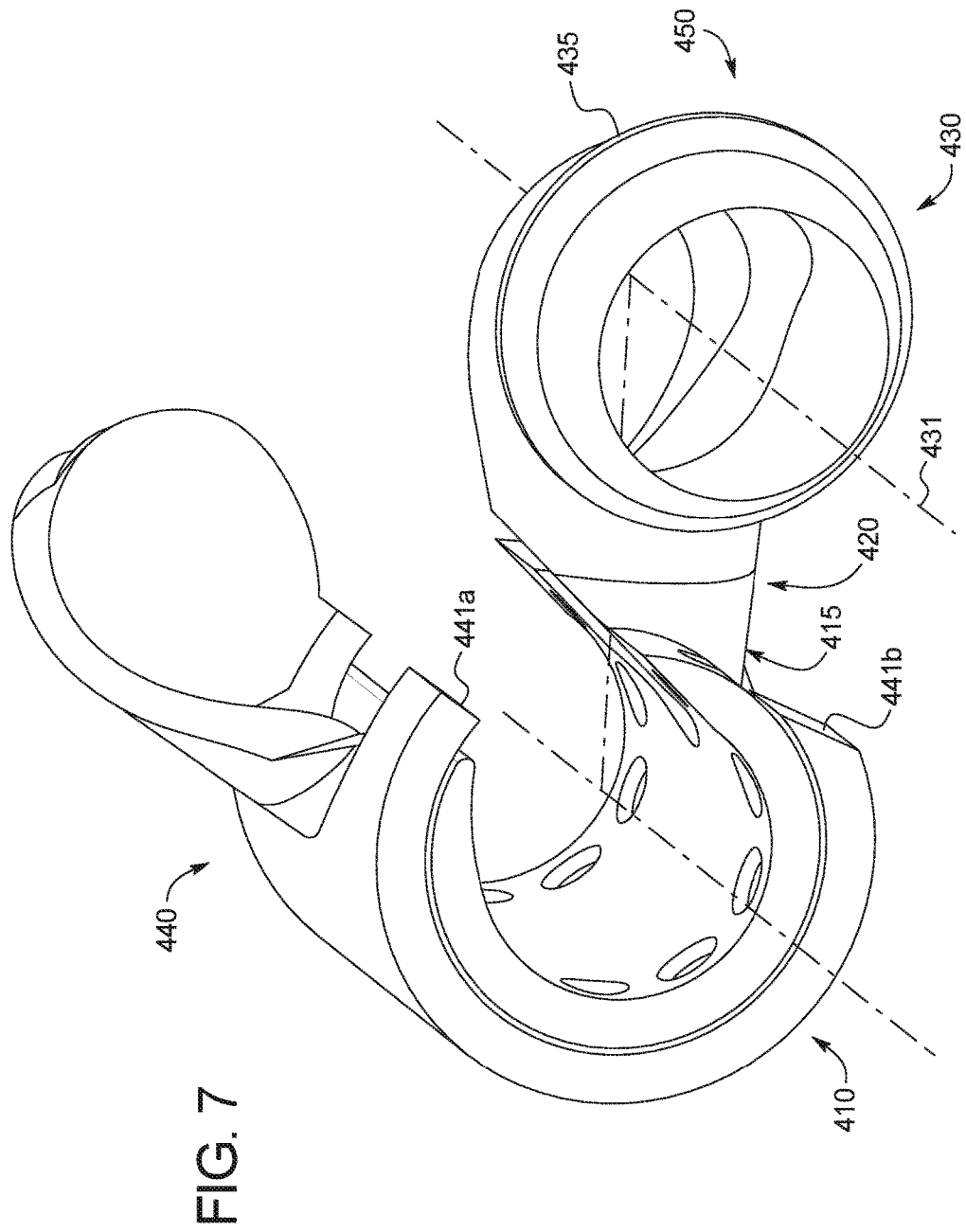
FIG. 7 illustrates a fourth embodiment of the medical implant device in a partially closed state.
Figure 8:
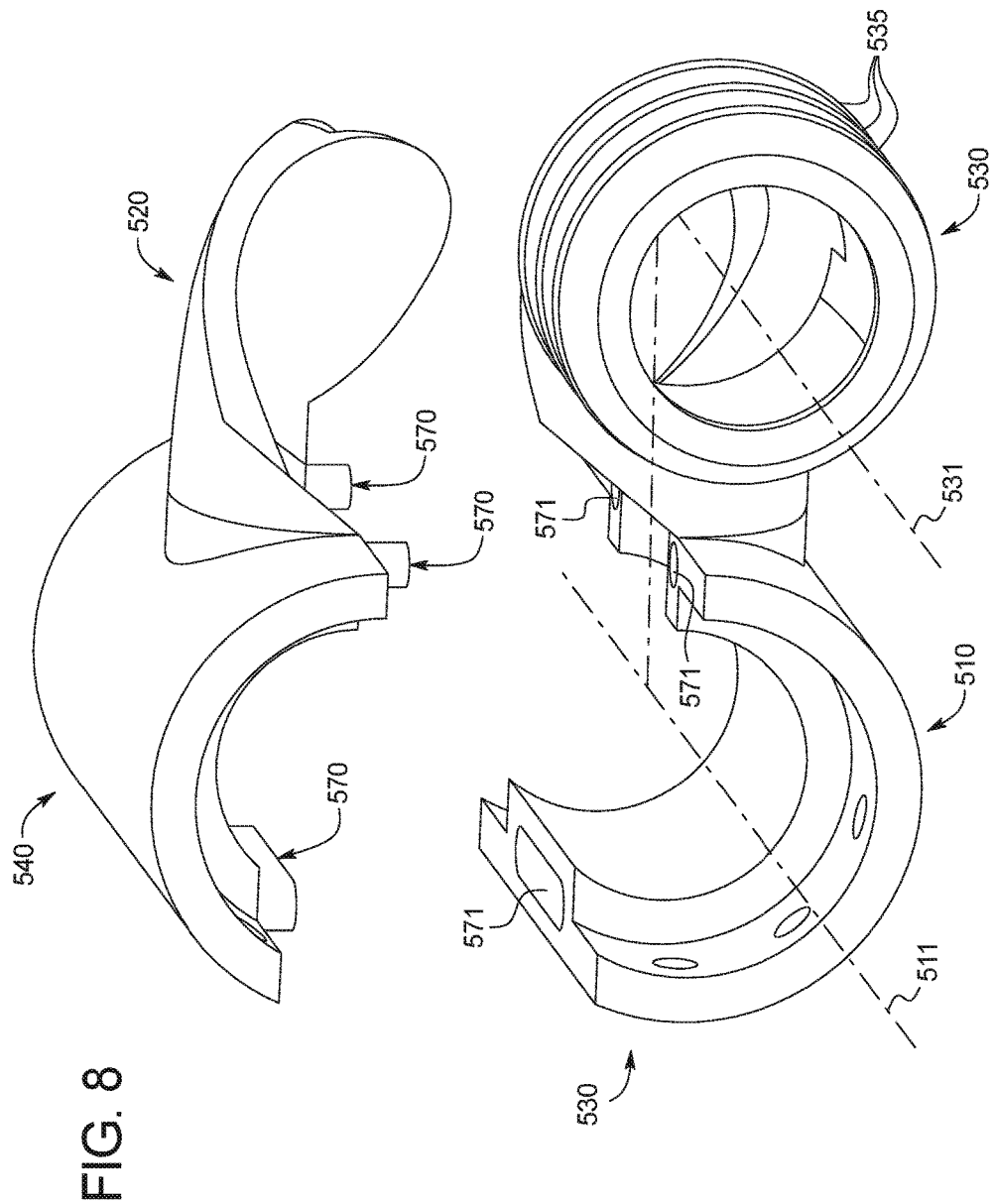
FIG. 8 illustrates a fifth embodiment of the medical implant device in an unassembled, or open, state.

The fourth and fifth embodiments illustrated in FIG. 7 and FIG. 8, respectively, like other implant devices may generally be thought of as having three different sections, an arterial section 410,510, a connector section 420,520, and a venous section 430,530.

The Fourth Embodiment

First, with reference to FIG. 7, the arterial section 410 of the implant device 400 may be similar to that of the second and third embodiments in that it may have top and bottom portions 440,450 where the top portion 440 fits to the bottom portion 450, providing a hinge, between an open and closed position. The arterial section 410 may be similar to that of the third embodiment except that it may have a square or uniform edge along both of its sides 441a, 441b. The venous section 430, likewise, may be the same as in the second embodiment except that, as illustrated, it may only provide for one rib with an outer diameter of 8-13 mm.

The connector section 420, like those of other embodiments, may be generally tubular in form when assembled and may provide a conduit between the arterial section 410 and venous section 430. Much of the tubular form of the connector section 420 may be provided by the top portion 440 and the bottom portion 450 may generally serve to connect the bottom portion 450 of the arterial and venous sections 410,430. The shape of the bottom portion 450 may provide access to the venous section 430 from a wide number of angles through both the distal and proximal ends 498, 499 of the implant device 400.

Differences in the Surgical Procedure

The surgical procedure may be similar to that of the second embodiment, involving similar preparation, and beginning the procedure in similar fashion, by exposing the surgical site and identifying the artery 491 and vein 492 most suitable for the procedure. With the appropriate implant device 400 chosen, the surgeon may ligate the vein 492, restricting blood flow into the surgical site, and may insert a needle and guide wire into the vein 492. With the guide wire in place, the needle may be removed and the surgeon may run a dilator on the guide wire to expand access to the vein 492. The dilator may also pass through the bottom portion 450 from its distal end along venous axis 431, so that the venous section 430 may be inserted into the vein 492 when the venous opening becomes sufficiently large. The surgeon may then secure the vein 492 (e.g., using a "purse string" suture) about the rib 435 on venous section 430 of the implant device 400.

The surgeon may also ligate the artery 491, slide the artery 491 into the bottom portion 450 of arterial section 410, and make an incision along its length such that blood will pass into the arterial connection region 415 once blood flow is resumed. With the artery 491 and vein 492 in place, the surgeon may place the top portion 440 in place and rotate it into the closed position, which may further secure the artery 491 within the arterial section 410. The surgeon may then transect the vein 492 such that the distal portion is released and the proximal portion remains secured to the venous section 430.

The Fifth Embodiment

Now with reference to the fifth embodiment illustrated in FIG. 8, the arterial section 510 may be generally tubular in form, having a region at the proximal and distal ends with an inner radius of 7-12 mm and a region extending there between having a narrower radius of 5-10 mm. The region with the narrower radius may extend along the arterial axis 511, in the portion of the arterial section 510 extending from the arterial connection region 515. The venous section 530 is similar to that illustrated in the second embodiment except that the venous section is 5-7 mm in length and has ribs 535 at uniform intervals (every 1-2 mm) along its length. The connector section 520 may be similar to that of the fourth embodiment in that it may allow access to the venous section 530 from its distal end.

In contrast to the other embodiments, the implant device 500 may be formed from top and bottom portions 540, 550 that are assembled together, rather than using a hinge. The arterial section 510 may be split in half along its length, and may provide one or more securing portions 570 extending from the top portion 540 of the arterial section 510 and mating with securing cavities 571 provided in the bottom portion 550.

Differences in the Surgical Procedure

The surgical procedure may be similar to that described above with reference to the fourth embodiment, involving similar preparation, and beginning the procedure in similar fashion, by exposing the surgical site and identifying the artery 591 and vein 592 most suitable for the procedure. With the appropriate implant device 500 chosen, the surgeon may ligate the vein 592, restricting blood flow into the surgical site, and may insert a needle and guide wire into the vein 592. With the guide wire in place, the needle may be removed and the surgeon may run a dilator on the guide wire to expand access to the vein 592. The dilator may also pass through the bottom portion 550 from its distal end along venous axis 531, so that the venous section 530 may be inserted into the vein 592 when the venous opening becomes sufficiently large. The surgeon may then secure the vein 592 (e.g., using a "purse string" suture) about a rib 535 on venous section 530 of the implant device 500.

The surgeon may also ligate the artery 591, place the artery 591 into the bottom hemisphere 550 of arterial section 510, and make an incision in the arterial wall along its length such that blood will pass into the arterial connection region 515 once blood flow is resumed. With the artery 591 and vein 592 in place, the surgeon may align the securing portions with the corresponding cavities and may secure the top and bottom portions 540,550. The surgeon may then transect the vein 592 such that the distal portion is released and the proximal portion remains secured to the venous section 530.

The surgical process and device described above may provide various benefits in the formation of an AVF, including, for example and without limitation, a reduction in the time of occlusion to the surgical site as the artery and vein may be aligned in advance. The implant device may also minimize the amount of lateral distance that the vein is moved and may minimize or eliminate 'swing stenosis.' Furthermore, as the implant device serves to secure the external portion of the artery and vein, the blood may be minimally exposed to foreign bodies (i.e., the tubing wall), with the limited exception of the connector section 102.

While the present invention is described herein in terms of particular embodiments, those skilled in the art will recognize that various modifications and improvements may be made to the invention without departing from the scope thereof. The explanations and illustrations presented herein are intended to acquaint others skilled in the art with the invention, its principles, and its practical application. Those skilled in the art may adapt and apply the invention in its numerous forms, as may be best suited to the requirements of a particular use. It will also be appreciated from the above that the fabrication of the unique structures herein and the operation thereof also constitute methods in accordance with the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments. Furthermore, the advantages described herein are not necessarily the only advantages of the invention and it is not necessarily expected that every embodiment of the invention will achieve all of the advantages described. Accordingly, the specific embodiments of the present invention set forth above are not intended to be exhaustive or limiting, and the scope of the invention should be determined not with reference to the above description, but should instead be determined with reference to the appended claims, along with the full scope of equivalents to which such claims are entitled.

What is claimed is:

1. A medical implant device for use in human body including an artery and a vein, comprising:
    an arterial section that is configured to secure the artery, the arterial section having an arterial lumen provided therein, the arterial section having an arterial axis extending from a proximal end to a distal end of the arterial section, the arterial axis being coaxial with the artery;
    a venous section that is configured to secure the vein, the venous section having a venous lumen provided therein, the venous section having a venous axis extending from a proximal end to a distal end of the venous section, the venous axis being coaxial with the vein; and
    a connector section, having a connecting lumen provided therein, that is configured to provide a fluid conduit between the arterial section and the venous section, extending between the arterial section and the venous section from an arterial connection region to a venous connection region, the connector section having an arterial connection axis in the arterial connection region and a venous connection axis in the venous connection region,
    wherein the venous section has an open configuration and a closed configuration, and the venous section forms a sealed inner cavity in the closed configuration.

2. The medical implant device of claim 1, wherein the arterial axis and the venous axis are parallel to one another.

3. The medical implant device of claim 1, wherein the arterial connection axis is perpendicular to the arterial axis, and wherein the venous connection axis is coaxial with the venous axis.

4. The medical implant device of claim 1, wherein the arterial section, the venous section and the connector section are generally tubular.

5. The medical implant device of claim 4, wherein the arterial section has an inner diameter between 5 mm and 10 mm, the venous section has an inner diameter between 3 mm and 5 mm, and the connector section has an inner diameter between 4 mm and 9 mm.

6. The medical implant device of claim 4, wherein the arterial section, the venous section and the connector section have the same inner diameter.

7. The medical implant device of claim 1, wherein the arterial section has an overall length between 10 mm and 25 mm, the venous section has an overall length between 5 mm and 10 mm, and wherein the connector section extends between 3 mm and 5 mm laterally and between 3 mm and 5 mm along its length.

8. The medical implant device of claim 1, wherein the proximal end of the venous section is configured to be placed inside the vein and secured to one or more ribs of the venous section, with the one or more ribs being configured to secure the venous section to the internal surface of the vein.

9. The medical implant device of claim 1, further comprising one or more fixation features radially spaced about the proximal end of the arterial and venous section and the distal end of the arterial section.

10. The medical implant device of claim 9, where the one or more fixation features comprise holes, barbs, meshes or cuffs.

11. The medical implant device of claim 9, where the one or more features are holes provided through the arterial and venous sections for use with sutures to secure the implant device to the artery and vein.

12. The medical implant device of claim 9, where the one or more features are cuffs attached to the implant device and configured to be secured to the artery and vein.

13. A medical implant device for use in human body including an artery and a vein, comprising:
   an arterial section that is configured to secure the artery, the arterial section having an arterial lumen provided therein, the arterial section having an arterial axis extending from a proximal end to a distal end of the arterial section, the arterial axis being coaxial with the artery;
   a venous section that is configured to secure the vein, the venous section having a venous lumen provided therein, the venous section having a venous axis extending from a proximal end to a distal end of the venous section, the venous axis being coaxial with the vein;
   a connector section, having a connecting lumen provided therein, that is configured to provide a fluid conduit between the arterial section and the venous section, extending between the arterial section and the venous section from an arterial connection region to a venous connection region, the connector section having an arterial connection axis in the arterial connection region and a venous connection axis in the venous connection region; and
   wherein the venous section is configured to externally secure the vein, and wherein the venous section has an open configuration and a closed configuration, and the venous section forms a sealed inner cavity in the closed configuration.

14. A medical implant device for use in human body including an artery and a vein, comprising:
   a top portion and a bottom portion that are complimentary to one another and are configured to join together to form:
      an arterial section that is configured to secure the artery, the arterial section having an arterial lumen provided therein, the arterial section having an arterial axis extending from a proximal end to a distal end of the arterial section;
      a venous section that is configured to secure the vein, the venous section having a venous lumen provided therein, the venous section having a venous axis extending from a proximal end to a distal end of the venous section; and
      a connector section, having a connecting lumen provided therein, that is configured to provide a fluid conduit between the arterial section and the venous section, extending between the arterial section and the venous section from an arterial connection region to a venous connection region, the connector section having an arterial connection axis in the arterial connection region and a venous connection axis in the venous connection region; and
   provide a fluid pathway from the arterial section, through the connector section and into the venous section,
   wherein the venous section has an open configuration and a closed configuration, and the top portion forms a sealed relationship in the venous section when the venous section is in the closed configuration.

15. The medical implant device of claim 14, wherein the bottom portion further comprises:
   an arterial opening in the bottom portion of the arterial section and two atraumatic exposed edges along the arterial opening for minimizing trauma to the external wall of the artery, wherein the two atraumatic exposed edges form a radial opening angle of between 50 degrees and 80 degrees.

16. The medical implant device of claim 14, wherein the bottom portion further comprises:
   a first venous opening in the bottom portion of the venous section and two atraumatic exposed edges along the first venous opening for minimizing trauma to the external wall of the vein, wherein the two atraumatic exposed edges form a radial opening angle of between 50 degrees and 80 degrees, and
   a second venous opening in the bottom portion of the connector section with the two atraumatic exposed edges along the second venous opening.

17. The medical implant device of claim 14, wherein the top portion is configured to form a sealed relationship in the connector section and a generally closed relationship in the arterial section.

18. The medical implant device of claim 16, wherein the top portion of the venous section and connector section comprises a protruded region configured to match the first and second venous opening in the bottom portion and has a surrounding tapered region that is configured to interface with the bottom portion to form a seal through the venous section.

19. The medical implant device of claim 15, wherein the top portion of the arterial section is generally tubular in form having a larger diameter than the bottom portion, the top portion of the arterial section having an arc angle of between 150 degrees and 200 degrees and providing closure to the arterial opening in the bottom portion.

20. The medical implant device of claim 14, further comprising a securing portion extending from the connector section and having a top portion and a bottom portion that are configured to be aligned and secured together.

* * * * *